(12) United States Patent
Voordouw et al.

(10) Patent No.: US 6,376,173 B1
(45) Date of Patent: Apr. 23, 2002

(54) REVERSE SAMPLE GENOME PROBING

(75) Inventors: Gerrit Voordouw, Calgary; Donald W. S. Westlake, Victoria; Phillip M. Fedorak, Edmonton, all of (CA)

(73) Assignee: University Technologies International Inc., Calgary (CA)

( * ) Notice: Subject to any disclaimer, the term of this patent is extended or adjusted under 35 U.S.C. 154(b) by 0 days.

(21) Appl. No.: 07/719,005

(22) Filed: Jun. 21, 1991

(51) Int. Cl.$^7$ .................................................. C12Q 1/68
(52) U.S. Cl. .............................. 435/6; 436/57; 436/63; 436/501
(58) Field of Search ................................ 435/6; 436/63, 436/57, 501; 935/76, 77, 78

(56) References Cited

U.S. PATENT DOCUMENTS 4,540,052 A * 9/1985 Hitzman ...................... 166/303

OTHER PUBLICATIONS

Kimmel; Methods in Enzymology, vol. 152, p 393–399, 1987.*
Chen et al. Chemical Abstracts Accession No. CA110(25): 228142y. Farming Zhuanli Shenqing Gongki Shuomingshu, CN 85109606, Jun. 17, 1987.*
Saiki et al Proc Natl Acad Sci USA, vol. 86 (Aug. 1989) 6230–6234.*
Wang et al. Biosis No. 88137187 Chin J Microbiol Immunol. (Beijing) 9(4) 1989. 261–264.*
Saiki et al, PNAS vol. 86, pp. 6230–6234, "Genetic Analysis of Amplified DNA With Immobilized Sequence–Specific Oligonucleotide Probes" Aug. 1989.
"Reverse spot molecular hybridization technique and a test kit for hepatitis B virus detection" Chen, Yuanqing; Gu, Jianren Shanghai Institute for Tumor—Faming Zhuanli Shenqing Gongkai Shuomingshu, 19 pp.

* cited by examiner

*Primary Examiner*—Kenneth R. Horlick
(74) *Attorney, Agent, or Firm*—Stevens, Davis, Miller & Mosher, LLP

(57) ABSTRACT

A reverse genome probe process for detecting the presence of selected microorganisms (which may be bacteria, fungi or viruses) consists of:

(a) affixing a nucleic acid preparation from each of the selected microorganisms to a solid surface;
(b) preparing a "reverse" probe by labelling a nucleic acid preparation obtained from the sample;
(c) contacting the reverse probe with the solid surface under conditions which permit hybridization; and
(d) detecting the presence of any reverse genome probe.

By using the "reverse" probe (i.e., a probe prepared from the sample, as opposed to a probe prepared from a selected microorganism), a single incubation may be used for the initial characterization of an unknown sample.

11 Claims, No Drawings

REVERSE SAMPLE GENOME PROBING

FIELD OF THE INVENTION

This invention relates to nucleic acid probes for the detection of microorganisms. More particularly, the invention relates to a "reverse probe" nucleic acid probe.

BACKGROUND OF THE INVENTION

Nucleic acid probes for the detection and analysis of microorganisms are known, although clinical applications of this technology are still comparatively rare.

These probes have clear potential value in the microbiology labs utilized in such disciplines as medicine, environmental and/or water resources engineering, agronomy and veterinary medicine. Certain probes and procedures have been developed for detecting the presence of microorganisms such as *Chlamydia trachomatis, Haemophilus ducreyi, Mycobacterium* and *Escherichia coli*, in clinical samples, environmental samples and the like.

A detailed review of gene probe technology is provided in the textbook "Gene Probes for Bacteria" (A. J. L. Macario and E. Conway de Macario, editors. Academic Press Inc. 1990. ISBN. 0-12-463000-6).

As a general overview, conventional gene probe techniques involve:

(a) selection of a nucleic acid probe (which may be based on the total nucleic acid of the species of interest; or some limited sequence thereof);

(b) affixing the nucleic acid from a sample onto a solid matrix (such as a nitrocellulose membrane);

(c) contacting the nucleic acid probe with the sample nucleic acid affixed on the matrix under conditions which permit hybridization; and (d) detection of hybridization (as hybridization is regarded as evidence of the presence of the probe species within the sample).

Two of the most well known procedures used to probe microorganisms are:

(a) Southern blot (in which the sample nucleic acid is isolated, purified, subjected to restriction endonuclease digestion, subjected to electrophoresis, denatured, affixed to a solid matrix, then hybridized while affixed to the matrix with a radioactively-labeled probe); and (b) dot or spot blot (in which lyzates of the sample, containing denatured nucleic acid, are affixed to the solid matrix without prior electrophoresis).

Thus, it will be apparent that the prior-art techniques require that the total nucleic acid from the sample be affixed to the matrix, in order to subsequently utilize a species specific probe. This procedure is very time consuming if it is desired to use a plurality of gene probes to attempt to characterize a sample (as a separate incubation is required for each gene probe employed).

The present invention mitigates certain of the disadvantages of the prior-art probe technology by reversing the sample/probe relationship.

SUMMARY OF THE INVENTION

Novel methods and compositions are provided for detecting the presence of a microorganism or a virus in a sample using nucleic acid isolated from the sample as a reverse genome probe. The method involves the steps of hybridizing the sample nucleic acid with a plurality of separately indentifiable nucleic acid standards prepared from organisms chosen based upon the origin of the sample, freeing the complexes of unbound sample and reagents, and detecting the complexes by means of a label attached to the sample nucleic acid. The indentity of the organism is obtained from the standard to which the sample nucleic acid hybridized. Optionally, the sample may be grown prior to analysis to increase the number of organisms. The method finds use in analyzing microorganism populations in environments where the microbial flora is poorly characterized.

Thus, in the broadest aspect of the present invention, a new and convenient method for the determination of the presence of more than one selected standard within a total microorganism sample is provided. In particular, the present invention provides:

Claim 1

In another embodiment of this invention, there is provided:

Claim to Master Solid Surface.

It will be appreciated that a "total" nucleic acid sample (i.e. a sample of the nucleic acid of the combined microorganisms present in the total sample) is employed as a reverse genome probe in the method of this invention.

As a further note of clarification regarding the difference between prior art gene probes and this invention, it will be recognized that the prior art probes may be prepared at and distributed from a central location (i.e. so that an end user provided with the probe then needs to prepare a filter or "solid surface" in order to complete the prior art probing process) whereas this invention permits the preparation of a master solid surface at a central location (so that an end user provided with a master solid surface needs only to prepare the reverse probe in order to undertake the process of this invention).

DETAILED DESCRIPTION

In accordance with the subject invention, methods and compositions are provided for indentifying a organism in a sample, particularly in a field sample from an uncharacterized microbial environmental such as an oil field. The presence of an organism may be detected using nucleic acid prepared from the sample itself as a reverse gene probe.

This invention is generally suitable for gene probing a wide variety of prokaryotic microorganisms, including bacteria and eukaryotic microorganisms, including fungi, as well as viruses. As will be readily recognized by those skilled in the art, different types of gene probes have different sets of advantages and disadvantages. Although this invention provides a means to conveniently provide an initial characterization of a complex specimen or sample, this convenience may come at a cost of not being able to distinguish between microorganisms having very similar genomes (i.e. this invention does not allow one to completely distinguish between species having strongly cross-hybridizing genomes. However, where closely related organisms with homologous cross-hybridizing genomes may be present in the sample, and it is desired to obtain more specific information, the technique may be combined with other techniques known to those skilled in the art to identify more specifically any closely related organisms.) Accordingly, the term "selected standard" as used herein includes both:

(a) a microorganism having a genome that doesn't cross-hybridize with any other; and (b) a group of microorganisms having homologous, cross-hybridizing genomes (i.e. such a group represents a single selected standard).

In other words, a given selected standard may simply be one microorganism or it may be a group of closely related microorganisms. Thus, a given selected standard is different from another selected standard if they have genomes with little or no cross-hybridization.

In spite of this limitation, it will be readily apparent that the present invention provides a rapid means for the initial characterization of a sample, because only a single incubation (rather than multiple incubations) is required after a suitable master filter has been prepared.

This is because the "reverse probe" used in this invention is prepared using the total nucleic acid from the sample (whereas the probe of the conventional prior art technique is prepared with nucleic acid from the selected or target species). From this, it follows that the master solid surface used in this invention has affixed thereto spots of nucleic acid from selected standards of interest (whereas, as noted above, the prior art techniques involve the use of a solid surface having affixed thereto total nucleic acid from the sample and hence require an incubation with each conventional probe being utilized).

Additionally, it has been surprisingly discovered that the total specimen nucleic acid (i.e. nucleic acid obtained directly from the sample, without first isolating the species therein) is suitable for use as a "reverse genome probe".

As noted above, the method of this invention generally involves three main steps:
1. Preparation of a Master Solid Surface.
2. Preparation of a Reverse Genome Probe.
3. Contacting the Reverse Genome Probe with the Master Solid Surface under conditions which permit hybridization.

Each of the above steps is described in detail below.

Master Solid Surface

The master solid surface of this invention is similar to the solid surface of prior art probes, except for the fundamental difference that the solid surface of this invention is "spotted" with nucleic acid from the selected standards of interest, whereas the prior art solid surface is spotted with nucleic acid from the sample.

The material of the master solid surface is not critical to the success of this invention. Any of the materials which may be used to prepare conventional gene probe solid surfaces are suitable. Non-limiting examples of these materials include nitrocellulose, glass and nylon (including modified nylon filters).

The use of nylon is preferred, for convenience.

The initial step in preparation of the master solid surface is to obtain the selected standards of interest.

Individual cultures of each of these selected standards must then be made. As will be readily appreciated by those skilled in the art, this will typically involve making cultures of the bacteria or fungi of interest, or growing the virus of interest on a suitable host.

For each of these individual cultures, the following steps must be completed:
(a) isolating and purifying a representative nucleic acid sample, and
(b) affixing the representative nucleic acid sample to the master solid surface. (Note: as used herein, the term nucleic acid is meant to include deoxyribronucleic acid (DNA), ribonucleic acid (RNA), or both, as the context may require).

The isolation of the nucleic acid sample can be completed using procedures well known to those skilled in conventional gene probe techniques. It is preferred to utilize the genomic DNA (i.e. the complete DNA) as the representative nucleic acid of the selected standards in the preparation of the master solid surface.

The preferred procedure to isolate and purify nucleic acid involves:
(a) harvesting the cells from the culture (by centrifugation or filtration);
(b) lysing the culture, preferably with a cell wall degrading enzyme (such as lysozyme) and a detergent such as sodium dodecyl sulfate (or "SDS") (optionally with the addition of Sarkosyl and ethylenediamine tetra-acetic acid (EDTA));
(c) treatment with enzymes (preferably proteinase K and/or ribonuclease A);
(d) solvent extraction (especially phenol and/or chloroform extraction); and
(e) precipitation (preferably with ethanol).

The resulting nucleic acid is subsequently dissolved in aqueous buffer in a defined concentration, denatured, spotted onto and affixed to a master solid surface.

As will be appreciated by those skilled in the art, the procedure used to affix the nucleic acid to the master solid surface will depend upon the type of solid material which is utilized.

For reasons of cost and efficiency, nylon is the preferred material for the master solid surface.

It will also be appreciated that the isolated, purified nucleic acid must be denatured (i.e. treated so as to separate the nucleic acid strands) prior to affixing it to the master filter.

The nucleic acid may be denatured, for example, by boiling or by treatment with sodium hydroxide (NaOH).

The resulting denatured nucleic acid is then affixed to the master solid surface, using conventional techniques. For a preferred nylon membrane master solid surface, this typically involves spotting a dilute solution of denatured nucleic acid from each of the species of interest at defined spots on the surface (i.e. so as to form a grid of the different selected species) followed by irradiation with ultraviolet light to link the denatured nucleic acid to the surface.

Preparation of Reverse Genome Probes

As previously noted, the reverse genome probes used in this invention are prepared using the total population of microorganisms present in the sample. Depending upon the application, it may be either necessary or desirable to increase the number of organisms present in the sample in order to have sufficient labeled nucleic acid to provide for a detectable signal. Accordingly, the sample may be grown in vitro using an appropriate nutrient medium to increase the microorganism population. Where the microorganism population in the sample has diverse nutrient requirements, aliquots of the sample may be grown in a plurality of nutrient media which contain different nutrients, for example carbon sources, and reverse nucleic acid probes prepared from each subculture. The total sample is subjected to the following steps to prepare the reverse genome probe:
(a) isolating and purifying the nucleic acid;
(b) labeling the nucleic acid.

Both of the isolation/purification and labeling steps can be completed using conventional procedures. The critical distinction over the prior art gene probe techniques is that the present invention requires the labeling of the entire nucleic acid of the sample, whereas the prior art technique labels only nucleic acid probes for the species of interest.

The preferred procedures for isolating and purifying the nucleic acid from the sample are essentially the same as the procedures used to isolate and purify the species-specific nucleic acid. The method of the present invention can be used for the detection of an organism in either the presence or absence of protein. However, when protein is present, an additional step to deproteinize the sample is desirable. Any conventional means can be used, for example phenol extraction, which does not adversely effect the integrity of the nucleic acid.

Generic methods of deproteinization may include mixing the sample with a suspension of glass particles in the presence of a high concentration of sodium iodide whereby DNA present in the sample is bound by the glass particles, isolating the glass particles, and then eluting the DNA with water or phosphate buffered saline. Glass particles may include finely ground glass beads (such as those sold under the name "GeneClean II" by BIO/CAN Scientific Inc.).

Another method which can be used is admixing a protein-containing sample with a proteolytic enzyme composition, comprising, for example, at least one of the enzymes pronase or proteinase K. Following the enzymatic treatment, hydrolyzed product is removed, for example, by centrifugation.

After protein is removed, the nucleic acid is denatured, for example by heating at 90–100° C., or treatment with sodium hydroxide or by other methods known to those skilled in the art. To prevent the nucleic acid from reannealing, the sample may be rapidly chilled or neutralized.

The isolated, purified nucleic acid from the sample is labeled to produce the reverse genome probe.

It is not intended to limit this invention to the use of any particular type of labeling procedure. To label the reverse nucleic acid probe, any of a variety of labels may be used including radioisotopes, fluorophors, or biotin. The label can be introduced to the nucleic acid by any standard enzymatic reaction, such as nick translation, or by terminal labeling, with $^{32}P$, $^{125}I$ or biotin-labeled deoxynucleotide triphosphates (dNTP). The label generally is introduced prior to denaturation of the nucleic acid.

For laboratory use, the preferred procedure is to radiolabel the total nucleic acid from the specimen/sample with $^{32}P$ by "nick translation". Nick translation is a well known labeling technique which generally involves "nicking" the nucleic acid (with deoxyribonuclease-1) and "extending the nicks" (with DNA polymerase) in the presence of the radiolabeled nucleic acid precursors so as to incorporate the radiolabeled precursors in the newly synthesized nucleic acid.

Although radiolabeling is preferred for laboratory use, the use of a non-radioactive labeling technique is preferred for field use.

Hybridization

The (attempted) hybridization of the reverse sample genome probe and the master solid surface is undertaken using the hybridization techniques which are commonly utilized with conventional genome probes.

For the preferred nylon membrane master filter/ radiolabeled reverse genome probe system, the hybridization technique simply involves contacting the master filter and the labeled, denatured reverse genome probe (preferably at an elevated temperature of between 40° C. and 70° C., for a period of 5 to 15 hours.

The probe is then removed from the filter, and the filter is carefully washed and air dried. X-ray film is contacted with and exposed to the probe, preferably for a period of 1 to 4 days. The presence of any dark spots on the developed X-ray film is indicative of hybridization between the reverse sample genome probe and the master filter (which, in turn, indicates that the species which was present on the master filter in the position(s) corresponding to the dark spot(s) on the X-ray film was present in the sample).

When it is desired to quantify the number of organisms present in a sample, at least one reference solution containing a known amount of nucleic acid representing a known number of organisms for hybridizing with a selected standard is treated identically to samples containing a known concentration of nucleic acid. At least one background solution containing no DNA is also included. The amount of label detectable in the background solution is subtracted from the amount of label detectable in the reference solution and the unknown sample. The relative amount of detectable label in the unknown sample thus indicates the relative amount of nucleic present in the sample and hence the number of organisms.

The reverse genome probe method finds use in analyzing microorganisms in environments with a microbial population that is not fully characterized. For example, a comparison of the organisms identified in corrosive and non-corrosive oil fields may aid in understanding the role of bacteria in the corrosion process. Also, a better understanding of the effectiveness of biocides on different bacterial populations in situ could be obtained when microorganism analysis is carried out sequentially on samples obtained from an oil field receiving biocide treatment. The technique may also be used to monitor the microbial diversity of an environment. Such information can be used to identify selected indicator organisms which are characteristic of a particular environment and whose presence can be monitored using more specific genome probes or other assays which will detect the specific organisms.

The method can also be generally applied toward the characterization or monitoring of microbial communities and other environments, including aquatic, soil, and animal. The technique may also find application in understanding and monitoring of large scale industrial processes that are catalyzed by microbial communities such as anaerobic sewage treatment. Suitable standards for a particular environment can be prepared from the organisms constituting the microbial flora in the environment under investigation. If the microbial population is analyzed without prior growth of sample, information concerning the population composition as it exists in nature may be obtained.

The following examples are offered by way of illustration and not by way of limitation.

EXAMPLES

In these examples, reverse genome probes are used to probe for the presence of selected sulfate-reducing bacteria ("SRB") in samples obtained from oil-fields. As the presence of SRB is often coincident with metal corrosion and/or oil field souring, a rapid technique to characterize samples from these environments may represent a useful tool in the prevention of corrosion and/or oil field souring.

Example 1

This example illustrates the preparation of a master solid surface having dot blots of 21 different "selected standard" microorganisms.

The selected standard microorganisms are identified in Table 1 by an alphanumeric name. The three letters of the name refer to the carbon source used for their first isolation (as described below). These selected standards are representative of SRB having genomes which do not strongly cross-hybridize with one another.

Three of the selected standards were obtained from culture collections, while the remaining 18 were isolated from oil field or sewage samples.

Each of the selected standards was individually cultured in a minimum of 80 ml of Pfennig's medium for several days. The Pfennig's medium also contained the carbon source indicated by the first three letters of the alphanumeric name (i.e. "Lac" refers to lactic acid, "Eth" refers to ethanol, "Ben" refers to benzoate, "Dec" refers to decanoic acid, "Pro" refers to propionic acid and "Ace" refers to sodium acetate) as the carbon sources present in the Pfennig's medium).

The preparation of Pfennig's medium initially involves making and mixing 5 different solutions. A sixth solution (which contains the carbon source) is then added to the 5 solution mixture. The ingredients of the solutions are given below:

| Solution 1: | |
|---|---|
| Distilled Water | 970 ml |
| $Na_2SO_4$ | 3 g |
| NaCl | 1.2 g |
| KCl | 0.3 g |
| $NH_4Cl$ | 0.3 g |
| $MgCl_2 \cdot 6H_2O$ | 0.4 g |
| $KH_2PO_4$ | 0.2 g |
| $CaCl_2 \cdot 2H_2O$ | 0.15 g |

Solution 1 is autoclaved for 30 min at 121° C. together with a plastic-coated magnetic bar. It is cooled under an atmosphere of 90% $N_2$ and 10% $CO_2$. Solutions 2–5 are added under stirring from sterile stock solutions.

| Solution 2: 1 ml trace element solution from the following autoclaved stock solution: | |
|---|---|
| Distilled Water | 993 ml |
| HCl (25%) | 6.5 ml |
| $FeCl_2 \cdot 4H_2O$ | 1.5 g |
| $H_3BO_3$ | 60 mg |
| $MnCl_2 \cdot 4H_2O$ | 100 mg |
| $CoCl_2 \cdot 6H_2O$ | 120 mg |
| $ZnCl_2$ | 70 mg |
| $NiCl_2 \cdot 6H_2O$ | 25 mg |
| $CuCl_2 \cdot 2H_2O$ | 15 mg |
| $Na_2MoO_2 \cdot 2H_2O$ | 25 mg |

| Solution 3: 1 ml selenite solution from the following autoclaved stock solution: | |
|---|---|
| Distilled Water | 1000 ml |
| NaOH | 0.5 g |
| $Na_2SeO_3$ | 3 mg |

| Solution 4: 30 ml $CO_2$-saturated Na-bicarbonate solution from the following sterile stock solution: | |
|---|---|
| Distilled Water | 100 ml |
| $NaHCO_3$ | 8.5 g |

Saturate with $CO_2$ and filter-sterilize into sterile, gas-tight, screw-capped bottles.

| Solution 5: 3 ml sodium sulfide solution from the following sterile stock solution: | |
|---|---|
| Distilled Water | 100 ml |
| $Na_2S \cdot 9H_2O$ | 12 g |

Autoclave in gas-tight screw-capped bottle under $N_2$ atmosphere.

After solutions 1–5 are mixed (e.g. with a magnetic stirrer), the pH is adjusted with sterile HCl or $Na_2CO_3$ solution (2 mol/litre) to the desired value. For enrichment cultures, pH 7.2 is satisfactory. The medium is distributed aseptically into 50 or 100 ml screw-capped bottles or 20 ml screw-capped tubes. This basal medium can be stored for several weeks before use.

| Solution 6: 1 ml of one of the following (sterile stock) solutions is added to the basal medium. The solutions below contain 100 ml water and the following amounts of the indicated carbon source: | |
|---|---|
| Na-acetate $3H_2O$ | 20 g |
| Propionic | 7 g (adjust to pH 9 with NaOH) |
| Lactic Acid | 15 g |
| Decanoic Acid | 5 g |
| Benzoic Acid | 5 g |
| Ethanol | 4 g |

After adding 1 ml of the carbon source solution, 0.1 ml of each of the following four (sterile stock) vitamin solutions is added to 100 ml culture medium. The vitamin solutions below contain 100 ml water and the following amounts of vitamin:

| Biotin | 1 mg |
|---|---|
| p-Aminobenzoic Acid | 5 mg |
| Vitamin $B_{12}$ | 5 mg |
| Thiamine | 10 mg |

After adding 0.1 ml of each of the above 4 vitamin solutions, 0.1 ml of a growth stimulating factor (GSF) solution is added to 100 ml of the culture medium. The GSF solution consists of 100 ml of water and

| Isobutyric Acid | 0.5 g |
|---|---|
| Valeric Acid | 0.5 g |
| 2-methyl-Butyric Acid | 0.5 g |
| Caproic Acid | 0.2 g |

-continued

| | |
|---|---|
| Succinic Acid | 0.6 g |
| NaOH (to adjust pH to 9) | |

After the above GSF solution is added, 0.1 ml of a Na-dithionite solution (consisting of 3 g $Na_2S_2O_4$ in 100 ml of $O_2$-free water) is added to the culture.

Cultures of each of the selected standards shown in Table 1 were grown for several days in a minimum of 80 ml of Pfennig's medium.

The nucleic acid (i.e. genomic DNA) was then isolated from each of the selected standards. The isolation procedures utilized are described in detail by Marmur, J. (1961, J. Mol. Biol. 3:208–218) and are also given below:

Isolation of Nucleic Acid

1. Place culture in 250 ml centrifuge bottle;
2. Cool on ice;
3. Centrifuge for 10 min at 10 k rpm (i.e. 10,000 revolutions per minute) in a Sorvall-type centrifuge;
4. Resuspend "pellet" (i.e. pellet refers to the cell concentrate) in 5 ml of 0.15 M NaCl, 0.1 M EDTA (pH=8);
5. Transfer to 50 ml centrifuge bottle, and centrifuge as in (3);
6. Resuspend pellet in 2.5 ml of NaCl/EDTA;
7. Add 0.2 ml of 25% (weight/volume, or "w/v") SDS;
8. Mix at 60° C. for 10 minutes;
9. Add 0.6 ml of 5 M $NaClO_4$;
10. Add 3 ml of $CHCl_3$/isoamyl alcohol (24/1, by volume);
11. Shake 30 minutes;
12. Centrifuge 5 min at 6 k rpm;
13. Remove supernatant;
14. Place in tube, layer 4 ml of ethanol on top;
15. Spool nucleic acid on glass rod;
16. Transfer to a tube containing 2 ml of 0.1×SSC; (where SSC is 0.15 M NaCl, 0.015 M $Na_3$-citrate, pH 7.2); and
17. Store in cold room.

NOTES

A. The (optional) addition of 1 mg of lysozyme between steps 6 and 7 assists with the procedures.
B. if no ethanol precipitate is obtained from step 14, employ the following procedures in lieu of steps 15–17:
   (18) Remove the $CHCl_3$/isoamyl alcohol (by pipette) and add 1 ml of ethanol/water (7/3, by volume);
   (19) Centrifuge pellet as in 3;
   (20) Suspend pellet in 100 µl of TE (where TE is 10 mM Tris-HCl, 0.1 mM EDTA, pH 8);
   (21) Digest with DNAase-free RNAase;
   (22) Digest with proteinase K;
   (23) Extract with phenol; and
   (24) Precipitate phenol extract as per 14;
   (25) Spool nucleic acid on glass rod (or collect by centrifugation);
   (26) Transfer nucleic acid to 0.2 ml of 0.1×SSC; and
   (27) Store in cold room.

Each of the isolated, purified nucleic acid standards was then dot-blotted onto a master solid surface as described below.

The master solid surface was a piece of nylon transfer membrane having dimensions of 10×8 cm, and a "net neutral charge" (sold under the trademark HYBOND N by Amersham Corporation of Arlington Heights, Ill.).

The nucleic acid standards were denatured by:
(a) diluting the nucleic acid to a concentration of 8 ng/µl with TE, where the concentration of nucleic acid is measured either by UV spectroscopy or fluorimetry in the presence of ethidium bromide; and
(b) adding a quarter volume of 0.5 M NaOH to the diluted standards (thus resulting in a final concentration of 6 ng/µl).

A volume of 2 µl of the resulting denatured, diluted nucleic acid standard solution was then spotted onto the master solid surface (i.e. for each of the 21 standards). A total of up to 50 master solid surfaces was typically prepared by one technician in a single session.

After all of the 21 selected standards had been spotted onto all of the master solid surfaces, the master solid surfaces were UV irradiated for 1 to 3 minutes with a Spectroline UV transilluminator, model C-62 (purchased from Fischer Scientific of Edmonton, Alberta), in order to affix the nucleic acid to the master solid surface.

The master solid surfaces were then washed in 6×SSC (where SSC is 0.15 M NaCl, 0.015 M $Na_3$-citrate, pH 7.2), dried, and stored at −20° C. until used.

Example 2

Preparation of Reverse Genome Probes

This example described the preparation of reverse genome probes.

Thirty-four (34) samples containing SRB were obtained from various oil field or waste water environments, as indicated in Table 2.

Each of these 34 samples was cultured in Pfenning's medium, using the procedures in Example 1. One to six separate cultures were prepared for each of the samples, using the different carbon sources identified in Table 2. A total of 77 cultures were made, as listed in Table 2.

The "total nucleic acid" from the cultures was then isolated using the procedures described in Example 1. It will be appreciated that the "total nucleic acid" present in the cultures of this example consisted of DNA that was representative of the total variety of microorganism(s) present in the field sample, whereas the isolated nucleic acid in Example 1 was representative of only the selected standard of interest.

The isolated total nucleic acid preparations were then used to fabricate reverse sample probes, by employing [α-$^{32}$P]dATP to radiolabel the nucleic acid by nick translation.

The following procedures were repeated for the nick translation of each of the reverse genome probes:

The following ingredients listed below were initially mixed together:
(a) 3 µl of total nucleic acid (as isolated and purified, having a nucleic acid concentration of 30 to 100 ng/µl);
(b) 5 µl of nick×10 buffer (where nick buffer consists of 50 mM Tris-HCl (pH 7.4), 10 mM $MgSO_4$, 0.1 mM dithiothreitol and 0.05 mg/ml of bovine serum albumin);
(c) 1 µl of dTTP (0.5 mM);
(d) 1 µl of dCTP (0.5 mM);
(e) 1 µl of dGTP (0.5 mM);
(f) 34 µl of water; and
(g) 3 µl of [α-$^{32}$P]dATP (3000 Ci/millimol, 10 mCi/ml).

The dTPP, dCTP and dGTP were obtained from Pharmacia LKB (Baie d'Urfe, Quebec) and the [α-$^{32}$P]dATP was obtained from Amersham Corporation (Arlington Heights, Ill.).

Five (5) µl of DNA-ase-1 (having a concentration of 5 mg/ml, obtained from Sigma Chemical Company of St. Louis, Mo) was then diluted 40,000 fold, and one µl of this dilution was added to the above ingredients.

One (1) µl of DNA polymerase-1 having a concentration of 2,000 units/ml (as defined by the supplier, Pharmacia LKB) was then added, and the labeling reaction was allowed to proceed for 9 hours at 10° C.

The labeled, reverse genome probe was then separated from unreacted [α-$^{32}$P]dATP by centrifugation (two minutes at 2,000 rpm through a column filled with molecular sieve resin (Sephadex G-25 resin, obtained from Pharmacia LKB) in TE. The labeled reverse sample genome probes were subsequently employed in Example 3.

Example 3

The example illustrates the use of reverse sample genome probes.

For each of the 77 cultures shown in Table 2, the reverse genome probe (described in Example 2) was denatured in a boiling water bath for 10 minutes and then hybridized with the master solid surfaces (as described in Example 1), and autoradiographed to determine which of the selected standards that were spotted on the master solid surfaces was present in the sample from which the reverse genome probe were made. [As a control, a spot of total nucleic acid from the sample was also denatured, affixed to the master solid surface by UV irradiation, and hybridized with reverse genome probe. The significance of this control spot is described in a [bracketed] section below].

Conventional high stringency (68° C.) procedures were employed for hybridization. A detailed discussion of these procedures is given, for example, by Voordouw G., et al (in 1989. J. Bacteriol. 171:3881–3889). The hybridization procedures used for each reverse genome probe are also listed below:

(a) Initially, the master solid surfaces were prehybridized in 6×SSC, 10×Denhardt solution (where Denhardt solution is 0.2 g of Ficoll, 0.2 g of polyvinyl-pyrrolidone, and 0.2 g of bovine serum albumin per 1 of water) and 0.2% (w/v) SDS for 15 minutes at 68° C.

(b) The denatured reverse genome probe was then added to the prehybridization solution (i.e. spread over the master solid surface) and hybridization was continued for 16 hours at 68° C.

(c) After hybridization, the master solid surfaces were washed in 6×SSC and 0.2% (w/v) SDS for 1 hour at 68° C.

(d) The master solid surfaces were then dried and autoradiographed (i.e. exposed to X-ray sensitive film, which film was subsequently developed).

If a selected standard was present in the sample from which the reverse genome probe was made (and it hybridized with the spot of standard or the master solid surface), the hybridization was visibly evident as a dark spot on the developed film. For example, sample number 1 of Table 2 was grown on Pfennig's medium using lactate as the carbon source (culture 1 in Table 2) and ethanol as the carbon source (culture 2 in Table 2). Reverse genome probing of these cultures indicate the presence of Lac 5 selected standard.

[Similarly, the "control" spot of total nucleic acid was also visibly evident on the film. It will be apparent that a failure to observe the control spot is indicative of a failure in the procedures, because the total nucleic acid sample of the control should hybridize with the reverse genome probe. Furthermore, it will also be apparent that a detectable control spot may be used as a reference for quantitative analysis, since the intensity of the control spot coloring is representative of the total microorganism population.]

TABLE 1

SELECTED STANDARDS

| Number | Selected Standard | Cross Hybridization | Identification |
|---|---|---|---|
| 1 | Lac1, 2 | — | A mixture of *D.vulgaris*subsp. *oxamicus* Monticello and *D. vulgaris* subsp *oxamicus*. |
| 2 | Lac3 | — | *D.desulfuricans* G200. |
| 3 | Lac4 | Lac5 | *Desulfovibrio* sp. |
| 4 | Lac5 | Lac4 | *Desulfovibrio* sp. |
| 5 | Lac6 | — | *Desulfovibrio* sp. |
| 6 | Lac7 | — | unidentified. |
| 7 | Lac8 | — | *Desulfovibrio* sp. |
| 8 | Lac10 | — | *Desulfovibrio* sp. |
| 9 | Eth1 | — | *Desulfovibrio* sp. |
| 10 | Ben1 | — | *Desulfovibrio* sp. |
| 11 | Ben2 | — | unidentified. |
| 12 | Dec1 | Dec3 | unidentified. |
| 13 | Dec2 | — | unidentified. |
| 14 | Dec3 | Dec1 | unidentified. |
| 15 | Pro1 | Pro3 | unidentified. |
| 16 | Pro2 | — | unidentified. |
| 17 | Pro3 | Pro1 | unidentified. |
| 18 | Pro4 | — | unidentified. |
| 19 | Ace1 | — | unidentified. |
| 20 | Ace2 | — | unidentified. |
| 21 | Ace3 | — | *Desulfobacterhydrogenophilus*. |

NOTES: Selected Standards were isolated from oil field or waste water samples (no. 4–20) or obtained from culture collections (no. 1, 2 and 21). The selected standards are named by the first three letters of the carbon source used for their isolation and cultivation on Pfennig's medium and an identifying number. Carbon sources used for the cultivation of selected standards were lactate, ethanol, propionate, benzoate, decanoate and acetate. Weak cross-hybridizations of a standard with others are indicated. Standards 3–5 and 7–10 were identified as SRB from the genus Desulfovibrio with the use of conventional Desulfovibrio specific gene probes.

TABLE 2

REVERSE SAMPLE GENOME PROBING

| N | n | Field Sample | Carbon Source | Identification |
|---|---|---|---|---|
| 1 | 1 | NOVA Husky #1A | Lactate | Lac5 |
| 2 | 1 | NOVA Husky #1A | Ethanol | Lac5 |
| 3 | 1 | NOVA Husky #1A | Decanoate | Dec3 |
| 4 | 1 | NOVA Husky #1A | Acetate | unidentified - a |
| 5 | 2 | NOVA Husky #1B | Ethanol | Lac1,2; Lac4; Lac5 |
| 6 | 3 | NOVA Husky #2 | Lactate | Lac5 |
| 7 | 3 | NOVA Husky #2 | Benzoate | Ben1 |
| 9 | 4 | NOVA Husky #3A | Lactate | Lac5 |
| 10 | 4 | NOVA Husky #3A | Ethanol | Lac4; Lac5; Ben1 |
| 11 | 4 | NOVA Husky #3A | Benzoate | Ben1 |
| 12 | 4 | NOVA Husky #3A | Propionate | Pro2 |
| 13 | 4 | NOVA Husky #3A | Decanoate | Dec3 |
| 14 | 4 | NOVA Husky #3A | Acetate | Ben1 |
| 15 | 5 | NOVA Husky #3B | Decanoate | Dec3 |
| 16 | 6 | NOVA Husky #4 | Lactate | Lac5; Lac4 |
| 17 | 6 | NOVA Husky #4 | Ethanol | Lac5 |
| 18 | 6 | NOVA Husky #4 | Benzoate | (Ben1) - b |
| 19 | 6 | NOVA Husky #4 | Acetate | unidentified - a |
| 20 | 7 | NOVA Husky #5 | Lactate | Lac5 |

TABLE 2-continued

REVERSE SAMPLE GENOME PROBING

| N | n | Field Sample | Carbon Source | Identification |
|---|---|---|---|---|
| 21 | 7 | NOVA Husky #5 | Ethanol | Lac4; Lac5; Ben1 |
| 22 | 7 | NOVA Husky #5 | Benzoate | Ben1 |
| 23 | 7 | NOVA Husky #5 | Propionate | Pro1 |
| 24 | 7 | NOVA Husky #5 | Decanoate | Dec3 |
| 25 | 7 | NOVA Husky #5 | Acetate | Ben1; Lac5 |
| 26 | 8 | NOVA Husky #6 | Lactate | Lac6 |
| 27 | 8 | NOVA Husky #6 | Ethanol | Ben1; Lac4; Lac7 |
| 28 | 8 | NOVA Husky #6 | Acetate | unidentified - a |
| 29 | 9 | NOVA Husky #7 | Lactate | Lac5 |
| 30 | 9 | NOVA Husky #7 | Ethanol | Lac5; Lac4; Ben1 |
| 31 | 9 | NOVA Husky #7 | Benzoate | Ben1 |
| 32 | 9 | NOVA Husky #7 | Propionate | Ben1 (Lac1,2;Lac5) |
| 33 | 9 | NOVA Husky #7 | Acetate | Ace1; Ben1 |
| 34 | 10 | NOVA Husky #8 | Lactate | Lac10 |
| 35 | 10 | NOVA Husky #8 | Ethanol | Lac4 |
| 36 | 10 | NOVA Husky #8 | Acetate | unidentified - a |
| 37 | 11 | NOVA Husky #10A | Lactate | Lac10 |
| 38 | 11 | NOVA Husky #10A | Ethanol | Lac10 |
| 39 | 12 | NOVA Husky #10A | Benzoate | Ben1 |
| 40 | 12 | NOVA Husky #10A | Propionate | Pro3 |
| 41 | 12 | NOVA Husky #10A | Acetate | Ben1 |
| 42 | 13 | NOVA Husky #10B | Ethanol | Lac5 |
| 43 | 14 | Shell #1A | Lactate | Lac4 |
| 44 | 14 | Shell #1A | Ethanol | Lac3 |
| 45 | 15 | Shell #1B | Lactate | Lac4 |
| 46 | 16 | Shell #2A | Ethanol | Lac6 |
| 47 | 17 | IPL #21 | Lactate | Lac3 |
| 48 | 17 | IPL #21 | Ethanol | Lac8 |
| 49 | 18 | IPL #22 | Lactate | Lac8 |
| 50 | 18 | IPL #22 | Ethanol | Lac8; Lac1,2 |
| 51 | 19 | IPL #27 | Ethanol | (Lac1,2; Lac8) |
| 52 | 19 | IPL #27 | Decanoate | (Dec1) |
| 53 | 20 | Virginia Hills #1 | Lactate | Lac4; Lac6 |
| 54 | 21 | Virginia Hills #2 | Lactate | Lac6 |
| 55 | 21 | Virginia Hills #2 | Ethanol | Lac4; Lac6; Ben1 |
| 56 | 21 | Virginia Hills #2 | Benzoate | Ben1 |
| 57 | 21 | Virginia Hills #2 | Decanoate | Dec1 |
| 58 | 22 | Virginia Hills #6 | Lactate | Lac6 |
| 59 | 23 | House Mountain #1 | Lactate | Lac4; Lac6 |
| 60 | 23 | House Mountain #1 | Benzoate | Ben1 |
| 61 | 24 | House Mountain #2 | Lactate | Lac4; Lac6 |
| 62 | 24 | House Mountain #2 | Benzoate | Ben1 |
| 63 | 24 | House Mountain #2 | Decanoate | Dec3 |
| 64 | 25 | House Mountain #3 | Lactate | Lac4; Lac6 |
| 65 | 25 | House Mountain #3 | Benzoate | Ben1 |
| 66 | 26 | House Mountain #4 | Lactate | Lac6 |
| 67 | 27 | House Mountain #6 | Lactate | Lac6; Pro4 |
| 68 | 28 | Sewage #1 | Ethanol | Eth1 |
| 69 | 29 | Sewage Culture B | Ethanol | Eth1 |
| 70 | 29 | Sewage Culture B | Benzoate | Ben2 |
| 71 | 29 | Sewage Culture B | Decanoate | Dec2 |
| 72 | 29 | Sewage Culture B | Acetate | unidentified - a |
| 73 | 30 | Banff Springs #1 | Lactate | Lac1,2 |
| 74 | 31 | Banff Springs #2 | Lactate | Lac1,2 |
| 75 | 32 | Uranium Mine Sludge A | Acetate | Ace2 |
| 76 | 33 | Uranium Mine Sludge B | Acetate | Ace2 |
| 77 | 34 | Uranium Mine Sludge C | Acetate | Ace2 |

[a]No identification could be made due to failed labeling of the sample DNA.
b1 Parentheses indicate very weak signal.
n refers to the sample number.
N refers to the culture number (i.e. more than one culture was prepared from some samples)

What is claimed is:

1. A process for detecting the presence of different selected standard microorganisms in a sample by reverse genome probing, wherein said process comprises the steps of:
   (A) preparing a master soled surface having affixed thereto isolated spots of genomic deoxyribonucleic acid from each of said different selected standard microorganisms by:
      (i) obtaining an individual culture of each of said selected standard microorganisms from an environment of interest,
      (ii) isolating a genomic deoxyribonucleic acid preparation from each of said individual cultures, and
      (iii) affixing each of said genomic deoxyribonucleic acid preparation from step (Aii) to said master solid surface,
   (B) preparing a reverse genome probe from said sample by:
      (i) isolating a total nucleic acid preparation from said sample by:
      (ii) labelling said total nucleic acid preparation,
   (C) contacting said master solid surface from step (A) with said reverse genome probe from step (B) under conditions permitting hybridization,
   (D) washing said master solid surface resulting from step (C) so as to remove non-hybridized reverse genome probe, and
   (E) detecting hybridized reverse genome probe.

2. The process of claim 1 wherein said environment of interest is an oil field environment and wherein said isolated spots of genomic deoxyribonucleic acid are a plurality of spots and wherein said selected standard microorganisms are a plurality of microorganisms.

3. The process of claim 1 wherein each of said selected standard microorganisms consist of at least one bacterium.

4. The process of claim 3 wherein each of said at least one bacterium is a sulfate-reducing bacterium.

5. The process of claim 1 wherein said labeling consists of radiolabeling.

6. The process of claim 1 wherein said master solid surface consists of a nylon membrane having a net neutral charge.

7. A master solid surface for use in detecting the presence of different selected standard microorganisms by reverse genome probing, said master solid surface having affixed thereto isolated spots of genomic deoxyribonucleic acid from each of said different selected standard microorganisms, wherein said selected standard microorganisms are isolated from an environment of interest.

8. The master solid surface of claim 7 wherein each of said selected standard microorganisms consists of at least one bacterium and wherein said isolated spots of genomic deoxyribonucleic acid are a plurality of spots and wherein said selected standard microorganisms are a plurality of microorganisms.

9. The master solid surface of claim 8 wherein each of said at least one bacterium is a sulfate reducing bacterium.

10. The master solid surface of claim 9 wherein said nucleic acid consists of genomic deoxyribonucleic acid.

11. The process of claim 1 wherein said selected standard microorganism include at least one virus.

* * * * *